United States Patent
Mozaffari et al.

(10) Patent No.: US 11,633,456 B2
(45) Date of Patent: Apr. 25, 2023

(54) COMPOSITIONS AND METHODS FOR PROMOTING HAIR GROWTH

(71) Applicant: Augusta University Research Institute, Inc., Augusta, GA (US)

(72) Inventors: Mahmood Mozaffari, Augusta, GA (US); Babak Baban, Augusta, GA (US)

(73) Assignee: Augusta University Research Institute, Inc., Augusta, GA (US)

(*) Notice: Subject to any disclaimer, the term of this patent is extended or adjusted under 35 U.S.C. 154(b) by 0 days.

(21) Appl. No.: 16/599,397

(22) Filed: Oct. 11, 2019

(65) Prior Publication Data

US 2020/0113970 A1 Apr. 16, 2020

Related U.S. Application Data

(60) Provisional application No. 62/745,695, filed on Oct. 15, 2018.

(51) Int. Cl.

| | | |
|---|---|---|
| *A61K 9/00* | (2006.01) | |
| *A61P 17/14* | (2006.01) | |
| *A61K 38/17* | (2006.01) | |
| *A61M 37/00* | (2006.01) | |
| *A61K 31/435* | (2006.01) | |
| *A61K 31/505* | (2006.01) | |

(52) U.S. Cl.
CPC .......... *A61K 38/179* (2013.01); *A61K 9/0021* (2013.01); *A61K 31/435* (2013.01); *A61K 31/505* (2013.01); *A61P 17/14* (2018.01); *A61M 37/0015* (2013.01); *A61M 2037/0061* (2013.01)

(58) Field of Classification Search
None
See application file for complete search history.

(56) References Cited

U.S. PATENT DOCUMENTS

| 6,074,843 | A * | 6/2000 | Hillman | C07K 14/4702 |
| | | | | 435/252.3 |
| 6,945,952 | B2 | 9/2005 | Kwon | |
| 10,059,748 | B2 * | 8/2018 | Dunia | A61P 25/16 |
| 10,076,649 | B2 | 9/2018 | Gilbert et al. | |
| 2003/0180302 | A1 * | 9/2003 | Wolf | A61K 48/00 |
| | | | | 424/146.1 |
| 2015/0033371 | A1 * | 1/2015 | Kobielak | A61K 35/36 |
| | | | | 800/13 |
| 2017/0196966 | A1 * | 7/2017 | Henderson | A61K 39/145 |

OTHER PUBLICATIONS

Ayroldi, E. et al., "Glucocorticoid-induced leucine zipper (GILZ): a new important mediator of glucocorticoid action," FASEB J, 23:3649-3658 (2009).
Baban, B. et al., "The role of GILZ in modulation of adaptive immunity in a murine model of myocardial infarction", Exp Mol Pathol 102(3):408-414 (2017).
Baban, B. et al., "Glucocorticoid-induced leucine zipper promotes neutrophil and T-cell polarization with protective effects in acute kidney injury," J Pharmacol Exp Ther, 367:483-493 (2018).
Beaulieu, E. et al., "Glucocorticoid-induced leucine zipper is an endogenous anti-inflammatory mediator in arthritis", Arthritis Rheum, 62(9):2651-2661 (2010).
Bereschenko, O. et al., GILZ promotes production of peripherally induced Treg cells and mediates the crosstalk between glucocorticoids and TGF-beta signaling, Cell Rep, 7(2):464-475 (2014).
Cannarile, L. et al., "Glucocorticoid-induced leucine zipper is protective in Th1-mediated models of colitis," Gastroenterology, 136:530-541 (2009).
D'Adamio, F. et al., "A new dexamethasone-induced gene of the leucine zipper family protest T lymphocytes from TCR/CD3-activated cell death", Immunity 7(6):803-812 (1997).
Jones, S.A. et al., "GILZ regulates Th17 responses and restrains IL-17 mediated skin inflammation," J Autoimmun, 61:73-80 (2015).
Riccardi, C. et al., "Glucocorticoid hormone-induced modulation of gene expression and regulation of T-cell death: role of GITR and GILZ, two dexamethasone-induced genes," Cell Death Differ, 6(12):1182-1189 (1999).
Ronchetti, S. et al., "GILZ as a mediator of the anti-inflammatory effects of glucocorticoids", Front Endocrinol (Lausanne), 6:170 (2015).
Srinivasan, M. et al., "Glucocorticoid-induced leucine zipper in central nervous system health and disease," Mol Neurobiol, 54(10):8063-8070 (2017).
Yang, N. et al., "Role of glucocorticoid-induced leucine zipper (GILZ) in inflammatory bone loss", PLoS One, 12(8):e0181133 (2017).

* cited by examiner

*Primary Examiner* — Marianne P Allen
(74) *Attorney, Agent, or Firm* — Smith, Gambrell & Russell; Judy Jarecki-Black

(57) ABSTRACT

Compositions and methods for treating hair loss are provided. One embodiment provides a microneedle composition, which when administered to the skin of a subject promotes hair growth. The microneedle compositions include an effective amount of glucocorticoid-induced leucine zipper (GILZ) protein having an amino acid sequence that has 99 or 100% identity to SEQ ID NO: 1, or fragment thereof to promote hair growth when administered to the skin of the subject and a bioerodible, biodegradable, or biosorbable polymer, wherein the composition is formulated as bioerodible, biodegradable, or bioabsorbable microneedles. In one embodiment the GILZ protein or fragment thereof is conjugated to a cell penetrating peptide. The cell penetrating peptide can be TAT GRKKRRQRRRPQ (SEQ ID NO:4) or a variant thereof.

5 Claims, 3 Drawing Sheets

Specification includes a Sequence Listing.

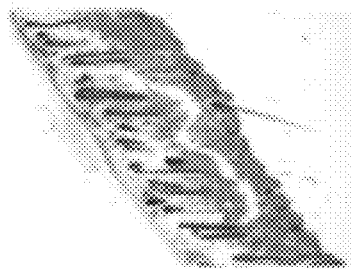
FIGURE 1E     FIGURE 1F     FIGURE 1G
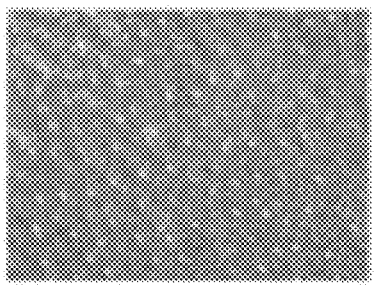
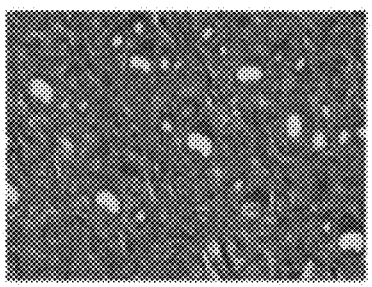
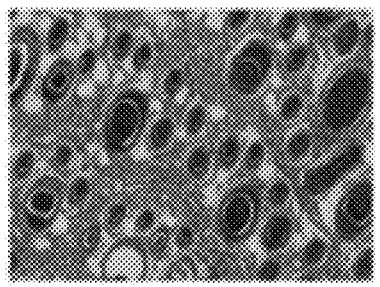
FIGURE 1H     FIGURE 1I     FIGURE 1J
FIGURE 1K     FIGURE 1L     FIGURE 1M
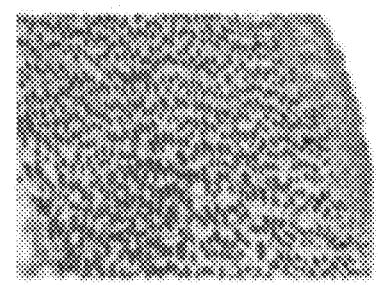
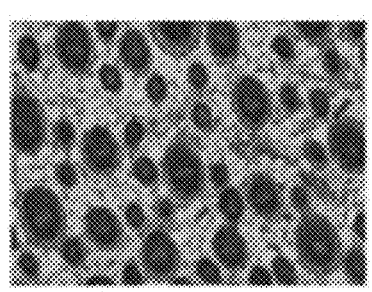
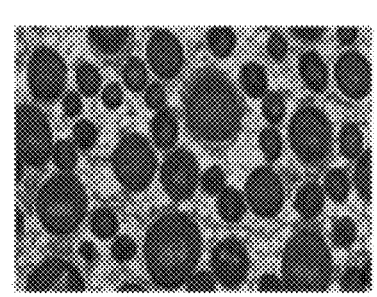
FIGURE 1N     FIGURE 1O     FIGURE 1P

COMPOSITIONS AND METHODS FOR PROMOTING HAIR GROWTH

CROSS-REFERENCE TO RELATED APPLICATIONS

This application claims benefit of and priority to U.S. Provisional Patent Application No. 62/745,695 filed Oct. 15, 2018 which is incorporated by reference in its entirety.

REFERENCE TO A SEQUENCE LISTING

The Sequence Listing submitted on Oct. 31, 2019 as a text file named "064466_102_seqlist_replacement" created on Oct. 31, 2019, and having a size of 10,431 bytes is hereby incorporated by reference pursuant to 37 C.F.R. § 1.52(e)(5).

TECHNICAL FIELD OF THE INVENTION

Aspects of the invention are generally related to compositions and methods for treating hair loss and promoting hair growth.

BACKGROUND OF THE INVENTION

Treating hair loss is lucrative market with men in the US spending approximately 1 billion dollars a year on shampoos, hair pieces, lotions, pills and follicle transplants. However, many of the shampoos, lotions, and conditioners only give the appearance of new hair. Instead of promoting hair growth, the lotions and shampoos contain degreasers that give the remaining hair a fuller appearance.

Existing drug treatments have mixed results. For example, minoxidil keeps hair from falling out if used early during hair loss. Only about 5 percent have been able to grow cosmetically beneficial hair using minoxidil. Another 30 percent typically grow a peach-fuzz type of covering. Additionally, minoxidil is not easy to use and in some cases is used two times a day. Most may try it, but then give up after a year. Finasteride has undesirable side effects. One serious side effect of finasteride is impotence and reduced libido.

Thus, it is an object of the invention to provide new compositions and methods for treating hair loss.

It is another object of the invention to provide compositions and methods for promoting hair growth.

SUMMARY OF THE INVENTION

Compositions and methods for treating hair loss are provided. One embodiment provides a microneedle composition, which when administered to the skin of a subject promotes hair growth. The microneedle compositions includes an effective amount of glucocorticoid-induced leucine zipper (GILZ) protein or fragment thereof to promote hair growth when administered to the skin of the subject and a bioerodible, biodegradable, or biosorbable polymer, wherein the composition is formulated as bioerodible, biodegradable, or bioabsorbable microneedles. In one embodiment the GILZ protein or fragment thereof is conjugated to a cell penetrating peptide. The cell penetrating peptide can be TAT YGRKKRRQRRR (SEQ ID NO:6) or a variant thereof. In one embodiment, the composition is stable for at least 3 weeks at 4° C. In one embodiment the GILZ is formulated as a microneedle patch.

Some embodiments include an additional therapeutic agent, for example an anti-inflammatory agent or an antibiotic. In some embodiments, the additional therapeutic agent is minoxidil, finasteride, or both. Typically, the GILZ composition is administered intradermally or transdermally.

Another embodiment provides a method for promoting hair growth in a subject in need thereof by administering an effective amount of a GILZ polypeptide or fusion protein thereof to promote hair growth in the subject at the site of injection.

BRIEF DESCRIPTION OF THE DRAWINGS

FIGS. 1E-1P are images of H&E stained skin samples of experimental groups.

DETAILED DESCRIPTION OF THE INVENTION

I. Definitions

Figure 1A:
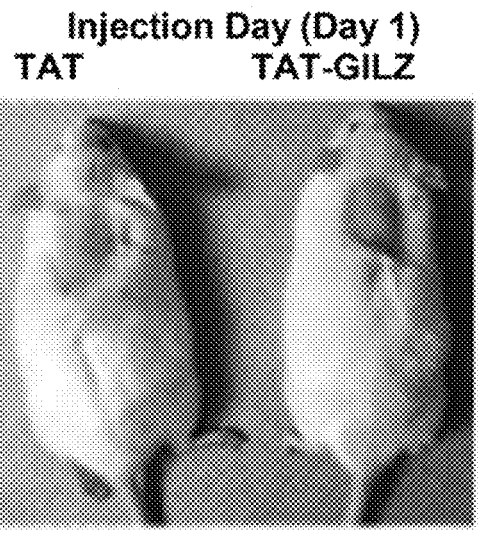
FIGS. 1A-1D are images of mice showing the clinical appearance of skin zones that were treated with TAT or TAT-GILZ in progression from injection day.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "treat," "treating," "treatment" and "therapeutic use" refer to the elimination, reduction or amelioration of one or more symptoms of hair loss. As used herein, a "therapeutically effective amount" refers to that amount of a therapeutic agent sufficient to inhibit or reduce hair loss or promote or induce hair growth, including but not limited to inducing or promoting new hair follicle growth or the activation of existing hair follicles.

The terms "individual", "host", "subject", and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

II. Compositions for Treating Hair Loss

Compositions and methods of treating hair loss are provided. One embodiment provides a pharmaceutical composition containing an effective amount of a GILZ protein or fragment thereof to inhibit or reduce hair loss or promote or induce hair growth, optionally fused to a cell penetrating peptide. An exemplary cell penetrating peptides is TAT. In some embodiments, the disclosed GILZ compositions include a second hair loss treatment, for example minoxidil, finestaride, or both.

In one embodiment, the GILZ compositions are formulated as microneedles. The microneedles can be biosorbable, hollow, porous, or a combination thereof. For example, one embodiment provide a microneedle patch having an array of microneedles that deliver GILZ proteins or fusion proteins thereof in an amount effective to inhibit or reduce hair loss or to promote or induce hair growth, including but not limited to inducing the formation of hair follicles or activating existing hair follicles to produce hair.

A. Hair Growth and Loss

Hair grows everywhere on the human skin except on the palms of the hands and the soles of the feet, but many hairs are so fine they're virtually invisible. Hair is made of a tough protein called keratin. A hair follicle anchors each hair into the skin. The hair bulb forms the base of the hair follicle. In the hair bulb, living cells divide and grow to build the hair shaft. Blood vessels nourish the cells in the hair bulb, and deliver hormones that modify hair growth and structure at different times of life.

Hair growth occurs in cycles including three phases: anagen, catagen, and telogen. In anogen, most hair is growing at any given time. Each hair spends several years in this phase. In catagen, the transitional phase, hair growth slows, and the hair follicle shrinks over a few weeks. In telogen, the resting phase, hair growth stops and the old hair detaches from the hair follicle. A new hair begins the growth phase, pushing the old hair out.

The causes of hair loss, also referred to as alopecia, are diverse, and genetic causes and androgen as a male hormone are considered to be important factors in the development of baldness. Hair loss can be temporary or permanent. Contributing factors and conditions to hair loss include genetic predisposition, hormonal imbalances, nutritional and vitamin deficiencies and chemotherapy, among others. It is presumed that the female pattern hair loss occurs in the same way as male pattern hair loss, but there is a difference in clinical appearance. Alopecia areata is considered to be an autoimmune disease. Telogen effluvium is temporary hair loss caused by severe physical and mental stresses such as endocrine diseases, malnutrition, drug use, birth, fever, and surgery and caused by a part of the hair which does not fill the growth period and falls into the dormant state.

B. Glucocorticoid-Induced Leucine Zipper Protein (GILZ)

Glucocorticoid-induced leucine zipper protein (GILZ) has been discovered to reduce hair loss, promote hair growth, promote formation of hair follicles, or a combination thereof. GILZ is a glucocorticoid-induced transcriptional regulatory protein. GILZ can homo- and hetero-dimerize with transcription factors such as NF-κB, Raf-1, TORC2, AP-1, Ras, and C/EBP, all of which are known to play a role in pro-inflammatory signaling. Other names for GILZ include but are not limited to tuberculosis sclerosis complex 22 (TCS22), DSIP-immunoreactive peptide, delta sleep-inducing peptide immunoreactor, TSC-22-like protein, and TSC-22 related protein.

1. Peptides

In some embodiments, the compositions and methods disclosed here contain GILZ proteins and/or peptides.

Sequences for human GILZ are known in the art. In one embodiment, the consensus amino acid sequence of GILZ is as follows:

```
                                         (SEQ ID NO: 1)
         10         20         30         40
MNTEMYQTPM EVAVYQLHNF SISFFSSLLG GDVVSVKLDN 50         60         70         80
SASGASVVAI DNKIEQAMDL VKNHLMYAVR EEVEILKEQI 90        100        110        120
RELVEKNSQL ERENTLLKTL ASPEQLEKFQ SCLSPEEPAP

130
ESPQVPEAPG GSAV
```
UniProt Q99576-1 which has been incorporated by reference in its entirety.

One embodiment provides an isolated or synthetic peptide, comprising an amino acid sequence having at least 75, 80, 85, 90, 95, 98, 99, or 100% sequence identity to SEQ ID NO: 1, optionally operatively linked to a cell penetrating peptide.

Another embodiment provides an isolated or synthetic peptide, comprising an amino acid sequence having at least 75, 80, 85, 90, 95, 98, 99, or 100% sequence identity to: MAQSKLDCRSPVGLDCCNCCLDLAHRSGLQRGSS-GENNNPGSPTVSNFRQLQEKLVFE NLNTDKLN-SIMRQDLEPVLRDPCYLENEGICNRNIDQTMLSILL-FFHSASGASVVAIDNK IEQAMDLVKNHLMYAVREEVEILKEQIRE-LVEKNSQLERENTLLKTLASPEQLEKFQSCL S PEEPAPESPQVPEAPGGSAV (SEQ ID NO:2) optionally operably linked to a cell penetrating peptide.

Another embodiment provides an isolated or synthetic peptide, comprising an amino acid sequence having at least 75, 80, 85, 90, 95, 98, 99, or 100% sequence identity to: GGWPSAVRAWEKAGSLPAEKEFLASFRAGAS-GASVVAIDNKIEQAMDLVKNHLMYAV REEVEIL-KEQIRELVEKNSQLERENTLLKTLASPEQLEKFQSCL-SPEEPAPESPQVPEAPGG SAV (SEQ ID NO:3) optionally operably linked to a cell penetrating peptide.

The GILZ peptide compositions can include non-naturally occurring peptides and peptide mimetics. The peptides can be any amino acid sequence that is identical to the entire sequence or a fragment of GILZ peptide. The peptides can vary in length. The peptides can be 5, 10, 15, 20, 25, 30, 35, 40, 45, 50 or 100 amino acids in length. Typically peptides will be in the range of 5-134 amino acids in length.

The disclosed GILZ peptides can be modified. As an example, a "methylated derivative" of a peptide refers to a form of the peptide that is methylated. Unless the context indicates otherwise, reference to a methylated derivative of a peptide does not include any modification to the base peptide other than methylation. Methylated derivatives can also have other modifications, but such modifications generally will be noted. For example, conservative variants of an amino acid sequence would include conservative amino acid substitutions of the based amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations.

Variants and derivatives are well understood by those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity. Conservative variants are also referred to herein as "conservative amino acid substitutions," "conservative amino acid variants," "conservative substitutions," and similar phrase. A "conservative derivative" of a reference sequence refers to an amino acid sequence that differs from the reference sequences only in conservative substitutions.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of the disclosed amino acid sequences can encompass sequences containing, for example, one, two, three, four or more amino acid substitutions relative to the reference sequence, and that such variants can include naturally and non-naturally occurring amino acid analogs.

2. Fusion Protein

In another embodiment, the GILZ peptide is part of a fusion protein. The GILZ peptide according to SEQ ID NO:1-3 can be coupled to other polypeptides, for example cell penetrating peptides, to form fusion proteins. Fusion polypeptides have a first fusion partner including all or a part of a human GILZ peptide fused to a second polypeptide directly or via a linker peptide sequence that is fused to the second polypeptide. In one embodiment, GILZ peptide is fused to a second polypeptide. The fusion proteins optionally contain a domain that functions to dimerize or multimerize two or more fusion proteins. The peptide/polypeptide linker domain can either be a separate domain, or alternatively can be contained within one of the other domains (first polypeptide or second polypeptide) of the fusion protein. Similarly, the domain that functions to dimerize or multimerize the fusion proteins can either be a separate domain, or alternatively can be contained within one of the other domains (first polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

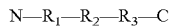

wherein "N" represents the N-terminus of the fusion protein, "C" represents the C-terminus of the fusion protein, "$R_1$" is a GILZ peptide, or functional variant or fragment thereof, "$R_2$" is an optional peptide/polypeptide linker domain, and "$R_3$" is a second polypeptide. In one embodiment, the second peptide is a cell penetrating peptide, for example a TAT peptide. Alternatively, $R_3$ is the GILZ peptide, or functional variant or fragment thereof and $R_1$ is the second polypeptide. In one embodiment, the fusion protein is a GILZ polypeptide fused to a cell penetrating peptide.

3. Cell Penetrating Peptides:

Exemplary cell penetrating peptides that can be used in the disclosed compositions include short amino acid sequences that are able to traverse biological membranes and deliver small molecules, proteins, viruses, and drugs inside of cells. In one embodiment, the cell penetrating peptides are 5-30 residues long. Cell penetrating peptides are classified as either protein derived cell penetrating proteins, chimeric cell penetrating proteins, or synthetic cell penetrating peptides.

Human immunodeficiency virus I (HIV 1) trans-activating protein (Tat) is a commonly utilized protein derived cell penetrating peptide. The α-helical domain of Tat protein spanning the residues 48 to 60 was found as the main determinant for cell internalization and nucleus translocation. Numerous cell penetrating peptides have been derived from the Tat dodecapeptide GRKKRRQRRRPQ (SEQ ID NO:4). Another common protein derived cell penetrating peptide is Penetratin peptide which has an amino acid sequence RQIKIWFQNRRMKWKK (SEQ ID NO:5).

Exemplary cell penetrating peptides include but are not limited to, YTA2, YTA4, TAT, Pen, R12, R16, r8, r12, R5, R7, Glu-Oct-6, Glu-Lys, 6-Oct, Phe-Oct-6, Asn-Oct-6, Tyr-Oct-6, RV24, TAT-NBD, TMTP1-TAT-NBD, AgNP-TAT, crotamine, R9-GO-203, iRGD-CDD, P7-1, P7-5, P7-6, P7-7, R7-KLA, KLA-R7, P1, P2, P3, P4, MG2A, CRGDK, L1, oligoarginine, GC/R8-Lip, p21-ELP1-Bac, Bac-ELP43, BacELP63, Bac-ELP122, TP10-SRC1LXXLL, R7-SRC1LXXLL, TP10-SRC1(1222-1245), R7-SRC1 (1222-1245), pep5-cpp, N-pep5-cpp, N2-pep5-cpp, N3-pep5-cpp, C2-pep5-cpp, C3-pep5-cpp, C4-pep5-cpp, C5-pep5-cpp, C6-pep5-cpp, C7-pep5-cpp, Ac-pep5-cpp, C24-LMWP, TAT-gelonin, TAT-BID, PTX-TAT-LP, PTX-C-TAT-LP, PTX-N-TAT-LP, B1, B1-Leu, B1-Lys, TAT-LP-PTX, T7/TAT-LP-PTX, T7-LP, TP, TP-biot1, TP-biot13, TP-10, TP10-biot1, P28, RALA peptide, TAT(47-57), Penetratin, pVEC, PEP-1, DS4.3, SR9, HR9, PR9, pf14, d-NTD, q-NTD, TH, MPG, polyarginine, polylysine, SAP, CyLoP-1, GALA, CADY, L17E, and MPPs.

In one embodiment, the cell penetrating peptides are selected from Penetratin or Antenapedia PTD RQIKIWFQNRRMKWKK (SEQ ID NO:5), TAT YGRKKRRQRRR (SEQ ID NO:6), SynB1 RGGRLSYS-RRRFSTSTGR (SEQ ID NO:7), SynB3 RRLSYSRRRF (SEQ ID NO:8), PTD-4 PIRRRKKLRRLK (SEQ ID NO:9), PTD-5 RRQRRTSKLMKR (SEQ ID NO:10), FHV Coat-(35-49) RRRRNRTRRNRRRVR (SEQ ID NO:11), BMV Gag-(7-25) KMTRAQRRAAARRNRWTAR (SEQ ID NO:12), HTLV-II Rex-(4-16) TRRQRTRRARRNR (SEQ ID NO:13), D-Tat GRKKRRQRRRPPQ (SEQ ID NO:14), R9-Tat GRRRRRRRRRPPQ (SEQ ID NO:15), Transportan GWTLNSAGYLLGKINLKALAALAKKIL (SEQ ID NO:16) chimera, MAP KLALKLALKLALALKLA (SEQ ID NO:17), SBP MGLGLHLLV-LAAALQGAWSQPKKKRKV (SEQ ID NO:18), FBP GALFLGWLGAAGSTMGAWSQPKKKRKV (SEQ ID NO:19), MPG ac-GALFLGFL-GAAGSTMGAWSQPKKKRKV-cya (SEQ ID NO:20), MPG(ΔNLS) ac-GALFLGFLGAAGSTMGAWSQPK-SKRKV-cya (SEQ ID NO:21), Pep-1 ac-KETWWETWW-TEWSQPKKKRKV-cya (SEQ ID NO:22), Pep-2 ac-KETWFETWFTEWSQPKKKRKV-cya (SEQ ID NO:23), poly Arginines, poly Lysines, and combinations thereof.

In some embodiments, chemical modifications to cell penetrating peptides can enhance therapeutic delivery. Synthetic cell penetrating peptides can be generated with chemical modifications to improve cellular uptake and provide cellular and sub-cellular specific targeting. Exemplary modifications include but are not limited to replacement of lysines with ornithine residues to confer resistance to cellular degradation, modification of the structure of peptides into dendrimers or cyclization, addition of phosphorylated groups and hydrophobic moieties to improve stability, and introduction of D-amino acids instead of L-amino acid configuration to protect peptides from degradation.

In one embodiment, a fusion protein obtained by fusion of GILZ with a cell penetrating peptide facilitates penetration of the fusion protein into cells so that their administration can modify cell functions in vivo. In a preferred embodiment, the fusion protein contains GILZ peptide (any one of SEQ ID NOs:1-3) fused to TAT peptide (SEQ ID NO:4). Methods of making TAT-GILZ fusion proteins are known in the art. For example, TAT-GILZ fusion protein can be constructed by inserting GILZ cDNA in the TAT-C vector to produce an in-frame fusion protein. See for example Cannarile, L., et al., *Gastroenterology*, 136:530-541 (2009).

4. Vectors

Another embodiment provides vectors encoding the GILZ proteins, polypeptides, fragments, variants and fusions thereof. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A. In one embodiment, a nucleic acid molecule encoding one of the disclosed polypeptides is present in a vector containing nucleic acids that encode one or more domains of an Ig heavy chain constant region, for example, having an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the proteins, polypeptides, fragments, variants and fusions thereof described herein.

The vectors described can be used to express the proteins, polypeptides, fragments, variants and fusions thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

C. Pharmaceutical Compositions

Pharmaceutical compositions containing the disclosed GILZ proteins, peptides, and fusion proteins thereof are provided. Pharmaceutical unit dosage forms of GILZ peptides and fusion proteins are suitable for mucosal (e.g., nasal, sublingual, vaginal, buccal, or rectal), topical, or transdermal administration to a patient. Examples of dosage forms include, but are not limited to: ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs.

Topical dosage forms of disclosed GILZ peptides and fusion proteins include, but are not limited to, liquids, creams, lotions, ointments, gels, waxes, pastes, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). In a preferred embodiment, the disclosed modified GILZ peptides are delivered to skin or mucosal wound tissue in a suitable topical dosage form.

For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, gels, waxes, pastes, liniments, salves, and the like, which are, if desired, sterilized or mixed with auxiliary agents (e.g., preservatives, stabilizers, wetting agents, buffers, or salts) for influencing various properties, such as, for example, osmotic pressure.

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the GILZ peptides of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466;465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of a GILZ peptide of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The disclosed GILZ compositions can also be administered by intralesional injection. Intralesional injection allows for delivery of a medication directly into a specific skin lesion to treat local tissues with minimal systemic effects.

The exact amount of the compositions administered to a wound can vary from subject to subject, depending on the species, age, weight and general condition of the subject, the severity of the wound being treated, and the mode of administration. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art.

For example, a typical daily dosage of a composition having a GILZ peptide or fusion protein used alone might range from about 1 µg/kg to up to 100 mg/kg of body weight or more per day, depending on the factors mentioned above. For example dosages can be about 0.01 to 5 mg/kg of the host body weight. In another embodiment, dosages can be 0.3 mg/kg body weight, 1 mg/kg body weight, 3 mg/kg body weight, 5 mg/kg body weight or 10 mg/kg body weight or within the range of 1-10 mg/kg body weight.

The application of topical formulations such as creams and ointments is often measured in fingertip units (FTUs). A FTU (about 500 mg) is the amount of medication needed to squeeze a line from the tip of an adult finger to the first crease of the finger. One FTU is enough to cover an area of skin the size of two adult hands with the fingers together. The recommended dosage will depend on what part of the body is being treated.

D. Microneedle Delivery and Systems Thereof

In one embodiment the GILZ polypeptides and fusions thereof are delivered using microneedles. Microneedles are known in the art and are described U.S. Pat. Nos. 6,945,952 and 10,076,649 which are incorporated by reference in their entirety. The microneedles can be solid, hollow, or porous. In some embodiments, the microneedles have a chamber in them that can be loaded with the GILZ polypeptides. The microneedles can be formed out of glass, metal, or polymers. In one embodiment the polymer is a biosorbable polymer that degrades over a period of time and releases the GILZ polypeptides. A representative biosorbable polymer is carboymethylcellulose. Typically, the GILZ polypeptides are combined with the biosorbable polymer and then formed into microneedles.

In some embodiments, the microneedles are assembled on to a patch. The patch can include an actuator to deliver the GILZ polypeptides into the skin at a site or hair loss or where hair growth is desired. In some embodiments, for example the when the GILZ polypeptides are formulated as biosorbable microneedles, the patch can simply be pressed into the skin to deliver the GILZ polypeptides as the microneedles are absorbed. Bioabsorption can occur over extended periods of time. In other embodiments, the microneedles are formed of a polymer that quickly dissolves when pressed into the skin.

III. Methods of Treating Hair Loss

Methods for treating hair loss using the disclosed GILZ polypeptide compositions are disclosed. One embodiment provides a method for promoting hair growth in a subject in need thereof by administering an effective amount of a GILZ protein, polypeptide, fragment thereof or fusion thereof to promote hair growth in the subject at the site of injection. The subject is typically a human male or female. In some embodiments, GILZ polypeptide or fragment thereof is conjugated to a cell penetrating peptide, for example TAT. Representative cell penetrating peptides include, but are not limited to Penetratin or Antenapedia PTD RQIKIWFQNRRMKWKK (SEQ ID NO:5), TAT YGRKKRRQRRR (SEQ ID NO:6), SynB1 RGGRLSYSRRRFSTSTGR (SEQ ID NO:7), SynB3 RRLSYSRRRF (SEQ ID NO:8), PTD-4 PIRRRKKLRRLK (SEQ ID NO:9), PTD-5 RRQRRTSKLMKR (SEQ ID NO:10), FHV Coat-(35-49) RRRRNRTRRNRRRVR (SEQ ID NO:11), BMV Gag-(7-25) KMTRAQRRAAARRNRWTAR (SEQ ID NO:12), HTLV-II Rex-(4-16) TRRQRTRRARRNR (SEQ ID NO:13), D-Tat GRKKRRQRRRPPQ (SEQ ID NO:14), R9-Tat GRRRRRRRRRPPQ (SEQ ID NO:15), Transportan GWTLNSAGYLLGKINLKALAALAKKIL (SEQ ID NO:16) chimera, MAP KLALKLALKLALALKLA (SEQ ID NO:17), SBP MGLGLHLLVLAAALQGAWSQPKKKRKV (SEQ ID NO:18), FBP GALFLGWLGAAGSTMGAWSQPKKKRKV (SEQ ID NO:19), MPG ac-GALFLGFLGAAGSTMGAWSQPKKKRKV-cya (SEQ ID NO:20), MPG(ΔNLS) ac-GALFLGFLGAAGSTMGAWSQPKSKRKV-cya (SEQ ID NO:21), Pep-1 ac-KETWWETWWTEWSQPKKKRKV-cya (SEQ ID NO:22), Pep-2 ac-KETWFETWFTEWSQPKKKRKV-cya (SEQ ID NO:23), poly Arginines, poly Lysines, and combinations thereof.

Typically, the GILZ polypeptide or fusion protein thereof is administered transdermally or intradermally, for example by a microneedles as discussed above.

Another embodiment provide a method for inducing the proliferation or maturation of hair follicles in skin by administering the disclosed GILZ polypeptides or fusion proteins thereof in an amount effective to induce proliferation of hair follicles, induce maturation of hair follicles, or both.

EXAMPLES

Example 1: GILZ-Fusion Proteins Promote Proliferation and Maturation of Hair Follicles Materials and Methods GST-TAT and GST-TAT-GILZ fusion proteins were delivered intradermally to an otherwise intact pre-shaved skin zone/area of mice. Accordingly, each mouse received 20 µl of phosphate buffer saline (PBS) which contained 2 µg of GST-TAT-GILZ and 1 µg of GST-TAT, hereinafter referred to as TAT-GILZ and TAT (n=3 mice/group). The selection of the dose is based on the 2 fold larger molecular weight of TAT-GILZ than TAT fusion protein (48 vs. 24 kDa). The treatment was carried out twice at one week intervals.

Results

Figure 1B:
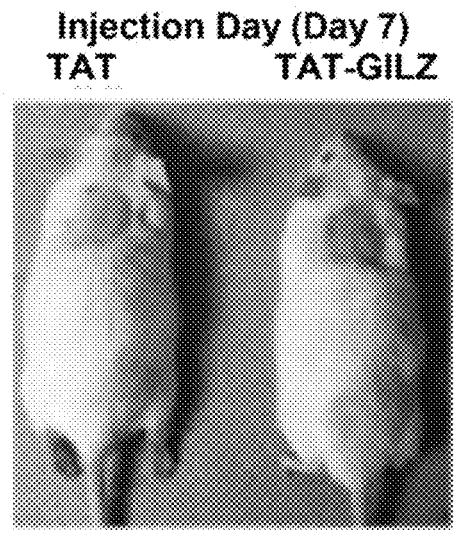
Figure 1C:
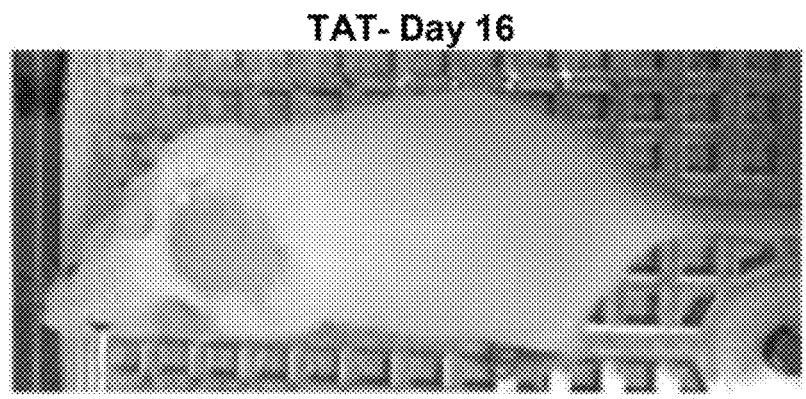
Figure 1D:
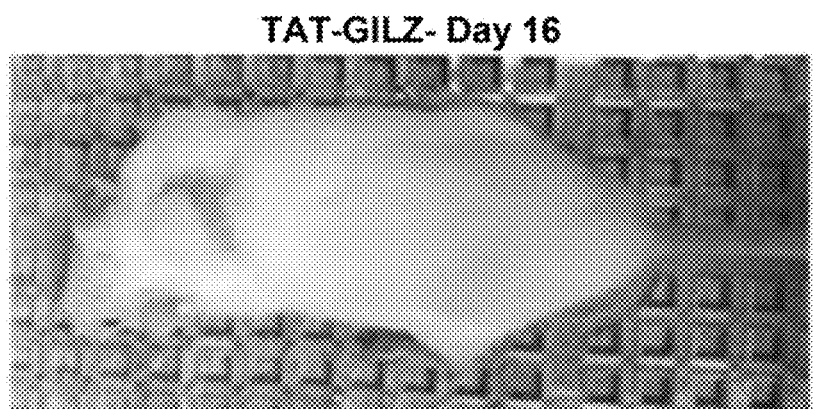
Figure 2A:
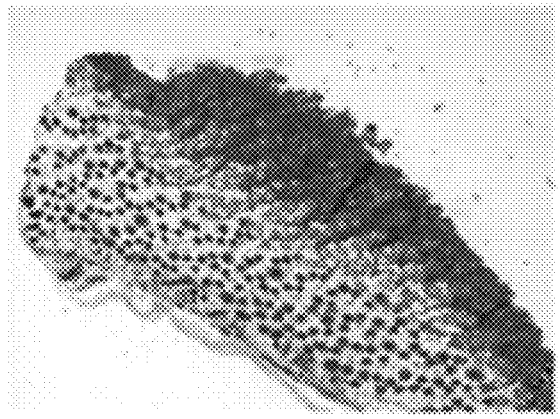
FIGS. 2A-2F are a panel of images of skin sections of TAT-GILZ treated mouse which were stained for Masson's Trichrome.
Figure 2B:
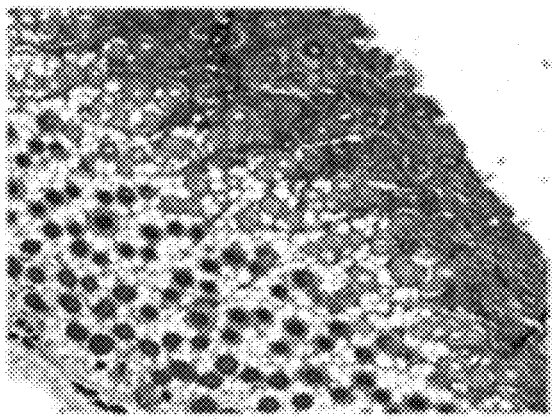
Figure 2C:
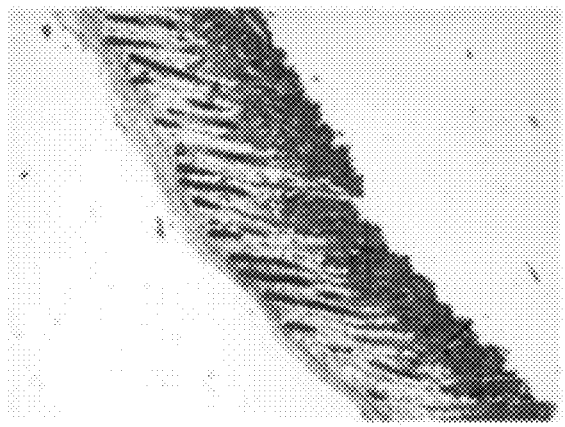
Figure 2D:
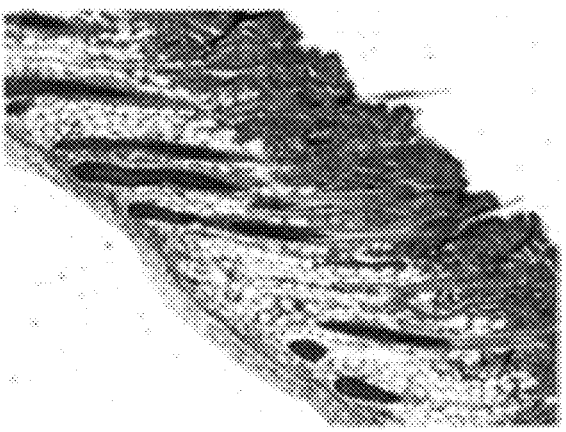
Figure 2E:
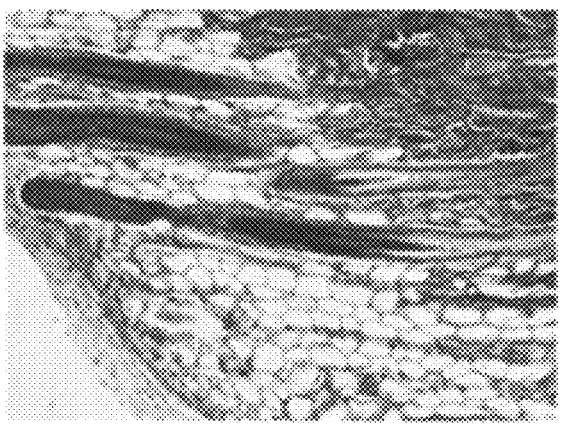
Figure 2F:
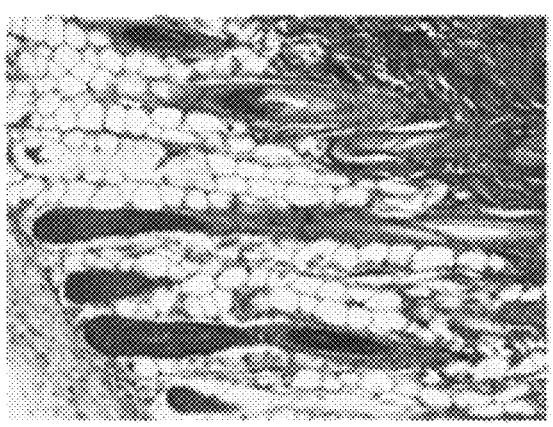

As shown in FIGS. 1A and 1B, mice that received either TAT or TAT-GILZ showed similar clinical appearance of shaved skin areas on the injection day (i.e., day 1) or 7 days after treatment. Interestingly, at day 16 after intradermal delivery of TAT or TAT-GILZ, mice treated with TAT-GILZ showed a remarkable increase in hair growth compared to TAT-treated mice whose skin area remained similar to day 7 (FIGS. 1C-1D). Skin was collected from both groups of mice, fixed in formalin, and prepared for histological analysis. As shown in FIGS. 1E-1P, histological features of skin between TAT- and TAT-GILZ-treated mice are very distinct. On the vertical sections, hair follicles seem to be primarily confined to the region of adipocytes (i.e., cells with clear cytoplasm) in the TAT-treated group. Also, in the TAT-group, transverse sections show hair follicles with "empty" spaces suggestive of "defective" hair follicle development.

Importantly, however, vertical sections of skin from TAT-GILZ-treated mice show elongated hair follicles that traverse the dermis and epidermis layers with obvious hair projections towards the skin surface. Examination of transverse sections of skin from TAT-GILZ-treated mice reveal a marked increase in hair follicles that appear fully developed and are very distinct from those of TAT-treated skin samples (i.e., transvers sections of TA-GILZ vs. TAT.

FIGS. 2A-2F show images of skin samples from TAT-GILZ treated mouse which were stained with Masson's Trichrome. The results are consistent with description of H&E-stained tissue sections although observations with Masson's Trichrome are even more striking due to inherent color contrast of the staining protocol.

The data show that the TAT-GILZ-induced proliferation and maturation of hair follicles culminating in hair growth.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for promoting hair growth in a subject in need thereof comprising:

administering by injection an effective amount of a GILZ protein having an amino acid sequence that has 99 or 100% sequence identity to SEQ ID NO:1 or fragment thereof to promote hair growth in the subject at the site of injection, wherein the GILZ protein or fragment thereof is conjugated to a cell penetrating TAT peptide according to SEQ ID NO:4, and wherein the administration of the GILZ protein or fragment thereof induces formation of hair follicles.

2. The method of claim 1, wherein the GILZ protein or fragment thereof is administered transdermally or intradermally.

3. The method of claim 2, wherein the GILZ protein or fragment thereof is administered by microneedles.

4. The method of claim 1, wherein the GILZ protein or fragment thereof is combined with a biosorbable polymer to form biodegradable polymeric microneedles, wherein the biodegradable polymeric microneedles are administered into the skin to deliver the GILZ protein or fragment thereof as the microneedles are absorbed.

5. A method for inducing hair follicle formation in skin comprising, administering by injection an effective amount of GILZ polypeptide having an amino acid sequence that has 99 or 100% sequence identity to SEQ ID NO:1 fused to a cell penetrating TAT peptide according to SEQ ID NO:4, into the skin of a subject in need thereof to induce hair follicle formation.

* * * * *

SEQUENCE LISTING

<160> NUMBER OF SEQ ID NOS: 23

<210> SEQ ID NO 1
<211> LENGTH: 134
<212> TYPE: PRT
<213> ORGANISM: Homo sapiens

<400> SEQUENCE: 1

Met Asn Thr Glu Met Tyr Gln Thr Pro Met Glu Val Ala Val Tyr Gln
1               5                   10                  15

Leu His Asn Phe Ser Ile Ser Phe Phe Ser Ser Leu Leu Gly Gly Asp
            20                  25                  30

Val Val Ser Val Lys Leu Asp Asn Ser Ala Ser Gly Ala Ser Val Val
        35                  40                  45

Ala Ile Asp Asn Lys Ile Glu Gln Ala Met Asp Leu Val Lys Asn His
    50                  55                  60

Leu Met Tyr Ala Val Arg Glu Glu Val Glu Ile Leu Lys Glu Gln Ile
65                  70                  75                  80

Arg Glu Leu Val Glu Lys Asn Ser Gln Leu Glu Arg Glu Asn Thr Leu
                85                  90                  95

Leu Lys Thr Leu Ala Ser Pro Glu Gln Leu Glu Lys Phe Gln Ser Cys
            100                 105                 110

Leu Ser Pro Glu Glu Pro Ala Pro Glu Ser Pro Gln Val Pro Glu Ala
        115                 120                 125

Pro Gly Gly Ser Ala Val
    130

<210> SEQ ID NO 2
<211> LENGTH: 200
<212> TYPE: PRT
<213> ORGANISM: Artificial Sequence
<220> FEATURE:
<223> OTHER INFORMATION: Synthetic peptide

<400> SEQUENCE: 2

Met Ala Gln Ser Lys Leu Asp Cys Arg Ser Pro Val Gly Leu Asp Cys
1               5                   10                  15

Cys Asn Cys Cys Leu Asp Leu Ala His Arg Ser Gly Leu Gln Arg Gly
            20                  25                  30

Ser Ser Gly Glu Asn Asn Asn Pro Gly Ser Pro Thr Val Ser Asn Phe
        35                  40                  45

Arg Gln Leu Gln Glu Lys Leu Val Phe Glu Asn Leu Asn Thr Asp Lys
    50                  55                  60

Leu Asn Ser Ile Met Arg Gln Asp Ser Leu Glu Pro Val Leu Arg Asp
65                  70                  75                  80

Pro Cys Tyr Leu Ile Asn Glu Gly Ile Cys Asn Arg Asn Ile Asp Gln
                85                  90                  95

Thr Met Leu Ser Ile Leu Leu Phe Phe His Ser Ala Ser Gly Ala Ser
            100                 105                 110

Val Val Ala Ile Asp Asn Lys Ile Glu Gln Ala Met Asp Leu Val Lys
        115                 120                 125

Asn His Leu Met Tyr Ala Val Arg Glu Glu Val Glu Ile Leu Lys Glu
    130                 135                 140

Gln Ile Arg Glu Leu Val Glu Lys Asn Ser Gln Leu Glu Arg Glu Asn
145                 150                 155                 160

Thr Leu Leu Lys Thr Leu Ala Ser Pro Glu Gln Leu Glu Lys Phe Gln
                165                 170                 175

Ser Cys Leu Ser Pro Glu Glu Pro Ala Pro Glu Ser Pro Gln Val Pro
            180                 185                 190

Glu Ala Pro Gly Gly Ser Ala Val
        195                 200

<210> SEQ ID NO 3
<211> LENGTH: 122
<212> TYPE: PRT
<213> ORGANISM: Artificial Sequence
<220> FEATURE:
<223> OTHER INFORMATION: Synthetic peptide

<400> SEQUENCE: 3

Gly Gly Trp Pro Ser Ala Val Arg Ala Trp Glu Lys Ala Gly Ser Leu
1               5                   10                  15

Pro Ala Glu Lys Glu Phe Leu Ala Ser Phe Arg Ala Gly Ala Ser Gly
            20                  25                  30

Ala Ser Val Val Ala Ile Asp Asn Lys Ile Glu Gln Ala Met Asp Leu
        35                  40                  45

Val Lys Asn His Leu Met Tyr Ala Val Arg Glu Glu Val Glu Ile Leu
    50                  55                  60

Lys Glu Gln Ile Arg Glu Leu Val Glu Lys Asn Ser Gln Leu Glu Arg
65                  70                  75                  80

Glu Asn Thr Leu Leu Lys Thr Leu Ala Ser Pro Glu Gln Leu Glu Lys
                85                  90                  95

Phe Gln Ser Cys Leu Ser Pro Glu Glu Pro Ala Pro Glu Ser Pro Gln
            100                 105                 110

Val Pro Glu Ala Pro Gly Gly Ser Ala Val
        115                 120

<210> SEQ ID NO 4
<211> LENGTH: 12
<212> TYPE: PRT
<213> ORGANISM: Human immunodeficiency virus type 1

<400> SEQUENCE: 4

Gly Arg Lys Lys Arg Arg Gln Arg Arg Arg Pro Gln
1               5                   10

<210> SEQ ID NO 5
<211> LENGTH: 16
<212> TYPE: PRT
<213> ORGANISM: Drosophila pseudoobscura

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 11
<212> TYPE: PRT
<213> ORGANISM: Human immunodeficiency virus type 1

<400> SEQUENCE: 6

Tyr Gly Arg Lys Lys Arg Arg Gln Arg Arg Arg
1               5                   10

<210> SEQ ID NO 7
<211> LENGTH: 18
<212> TYPE: PRT
<213> ORGANISM: Artificial Sequence

```
<220> FEATURE:
<223> OTHER INFORMATION: Synthetic peptide- SynB1

<400> SEQUENCE: 7

Arg Gly Gly Arg Leu Ser Tyr Ser Arg Arg Phe Ser Thr Ser Thr
1               5                   10                  15

Gly Arg

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide- SynB3

<400> SEQUENCE: 8

Arg Arg Leu Ser Tyr Ser Arg Arg Arg Phe
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide- PTD-4

<400> SEQUENCE: 9

Pro Ile Arg Arg Arg Lys Lys Leu Arg Arg Leu Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide- PTD-5

<400> SEQUENCE: 10

Arg Arg Gln Arg Arg Thr Ser Lys Leu Met Lys Arg
1               5                   10

<210> SEQ ID NO 11
<211> LENGTH: 15
<212> TYPE: PRT
<213> ORGANISM: flock house virus

<400> SEQUENCE: 11

Arg Arg Arg Arg Asn Arg Thr Arg Arg Asn Arg Arg Arg Val Arg
1               5                   10                  15

<210> SEQ ID NO 12
<211> LENGTH: 19
<212> TYPE: PRT
<213> ORGANISM: Brome mosaic virus

<400> SEQUENCE: 12

Lys Met Thr Arg Ala Gln Arg Arg Ala Ala Ala Arg Arg Asn Arg Trp
1               5                   10                  15

Thr Ala Arg

<210> SEQ ID NO 13
<211> LENGTH: 13
<212> TYPE: PRT
<213> ORGANISM: Human T-cell lymphotropic virus type 1
```

```
<400> SEQUENCE: 13

Thr Arg Arg Gln Arg Thr Arg Arg Ala Arg Arg Asn Arg
1               5                   10

<210> SEQ ID NO 14
<211> LENGTH: 13
<212> TYPE: PRT
<213> ORGANISM: Human T-cell lymphotropic virus type 2

<400> SEQUENCE: 14

Gly Arg Lys Lys Arg Arg Gln Arg Arg Arg Pro Pro Gln
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide- R9-Tat

<400> SEQUENCE: 15

Gly Arg Arg Arg Arg Arg Arg Arg Arg Arg Pro Pro Gln
1               5                   10

<210> SEQ ID NO 16
<211> LENGTH: 27
<212> TYPE: PRT
<213> ORGANISM: Artificial Sequence
<220> FEATURE:
<223> OTHER INFORMATION: Synthetic peptide- transportan

<400> SEQUENCE: 16

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide- MAP

<400> SEQUENCE: 17

Lys Leu Ala Leu Lys Leu Ala Leu Lys Leu Ala Leu Ala Leu Lys Leu
1               5                   10                  15

Ala

<210> SEQ ID NO 18
<211> LENGTH: 27
<212> TYPE: PRT
<213> ORGANISM: Artificial Sequence
<220> FEATURE:
<223> OTHER INFORMATION: Synthetic peptide- Streptavidin-binding peptide

<400> SEQUENCE: 18

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 19
<211> LENGTH: 27
```

```
<212> TYPE: PRT
<213> ORGANISM: Artificial Sequence
<220> FEATURE:
<223> OTHER INFORMATION: Synthetic peptide- Folate binding protein
      peptide

<400> SEQUENCE: 19

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 20
<211> LENGTH: 27
<212> TYPE: PRT
<213> ORGANISM: Artificial Sequence
<220> FEATURE:
<223> OTHER INFORMATION: Synthetic peptide- MPG peptide

<400> SEQUENCE: 20

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 21
<211> LENGTH: 27
<212> TYPE: PRT
<213> ORGANISM: Artificial Sequence
<220> FEATURE:
<223> OTHER INFORMATION: Synthetic peptide- MPG (delta NLS)

<400> SEQUENCE: 21

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide- Pep 1

<400> SEQUENCE: 22

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 23
<211> LENGTH: 21
<212> TYPE: PRT
<213> ORGANISM: Artificial Sequence
<220> FEATURE:
<223> OTHER INFORMATION: Synthetic peptide- Pep 2

<400> SEQUENCE: 23

Lys Glu Thr Trp Phe Glu Thr Trp Phe Thr Glu Trp Ser Gln Pro Lys
1               5                   10                  15

Lys Lys Arg Lys Val
            20
```